United States Patent [19]
Knight et al.

[11] Patent Number: 4,753,530
[45] Date of Patent: Jun. 28, 1988

[54] ANALYTICAL OPTICAL INSTRUMENTS

[75] Inventors: John H. G. Knight, New Malden; David Griffiths, Claygate, both of England

[73] Assignee: Oriel Scientific Ltd., England

[21] Appl. No.: 766,399

[22] Filed: Aug. 16, 1985

Related U.S. Application Data

[63] Continuation-in-part of Ser. No. 293,895, Aug. 18, 1981, abandoned.

[30] Foreign Application Priority Data

Aug. 21, 1980 [GB] United Kingdom ............... 8027319

[51] Int. Cl.$^4$ .............. G01N 21/64; G01N 21/31; G01N 21/49; G01N 21/55
[52] U.S. Cl. ............................... 356/73; 250/227; 356/318; 356/435; 356/448
[58] Field of Search ............. 356/317, 318, 417, 440, 356/435, 73; 29/3, 895; 250/227

[56] References Cited

U.S. PATENT DOCUMENTS

| | | | |
|---|---|---|---|
| 2,892,378 | 6/1959 | Canada | 250/574 X |
| 3,141,094 | 7/1964 | Strickler | 250/574 |
| 3,543,087 | 11/1970 | Saiger et al. | 356/23 |
| 3,564,264 | 2/1971 | Karuhn | 250/574 |
| 3,666,362 | 5/1972 | Chance | 356/320 |
| 3,807,875 | 4/1974 | Fischer et al. | 356/432 |
| 3,810,696 | 5/1974 | Hutchins, Jr. | 356/435 |
| 3,906,241 | 9/1975 | Thompson | 250/574 |
| 3,963,351 | 6/1976 | Chance et al. | 356/317 |
| 3,973,849 | 8/1976 | Jackson et al. | 356/308 X |
| 3,986,777 | 10/1976 | Roll | 250/227 X |
| 4,040,743 | 8/1977 | Villaume et al. | 356/73 |
| 4,076,421 | 2/1978 | Kishner | 356/320 |
| 4,152,075 | 5/1979 | Rellstab et al. | 250/227 X |
| 4,178,917 | 12/1979 | Shapiro | 356/317 |
| 4,240,751 | 12/1980 | Linnecke et al. | 250/227 X |
| 4,290,433 | 9/1981 | Alfano | 356/318 X |
| 4,293,225 | 10/1981 | Wheaton et al. | 356/417 |

FOREIGN PATENT DOCUMENTS

| | | |
|---|---|---|
| 1927330 | 1/1970 | Fed. Rep. of Germany . |
| 1959612 | 6/1971 | Fed. Rep. of Germany . |
| 2264433 | 5/1974 | Fed. Rep. of Germany . |
| 1589461 | 5/1970 | France . |
| 1054767 | 1/1967 | United Kingdom . |

OTHER PUBLICATIONS

German Article Found in Publication, Bio Medizin Ische Technik, 1975.
DiGiacomo, "Variable Angle Reflectometer", IBM Tech. Disc. Bulletin, vol. 20, #11A, Apr. 1979, pp. 4509-4510.

Primary Examiner—Vincent P. McGraw
Attorney, Agent, or Firm—Hall, Myers & Rose

[57] ABSTRACT

An optical measuring system for measuring in situ by means of one or more fiber-optic probes reflection absorption fluorescence, phosphorescence and turbidity of a fluid or (for all but the last measurement) of a fluid-solid interface. High intensity pulsed light is conveyed to the measurement site by a fiber-optic cable and is given a specific direction at the site by means of the geometry of the probe, reaction light resulting from the stimulating light pulse is discriminated by the geometry of the probe, or another probe, and is returned via a further fiber-optic cable to a measurement system which is enabled to sense the returning light only for the duration of the light pulse. The measurement system comprises means for sensing the relative intensity of the stimulating light pulse and for deriving a signal at least representative of the ratio of the magnitude of the quality sensed, by means of the probe, and the relative intensity of the stimulating light pulse. In one embodiment a unitary probe has three light channels, one conveying light to the site, one conveying light to the measurement system at least representative of the stimulating light intensity at the side and the last providing to the measurement system a signal representative of the magnitude of the quality of interest.

25 Claims, 7 Drawing Sheets

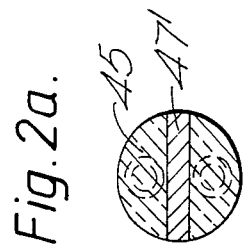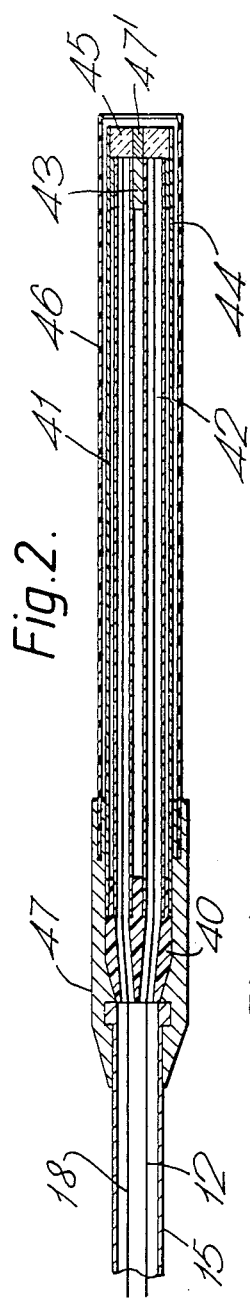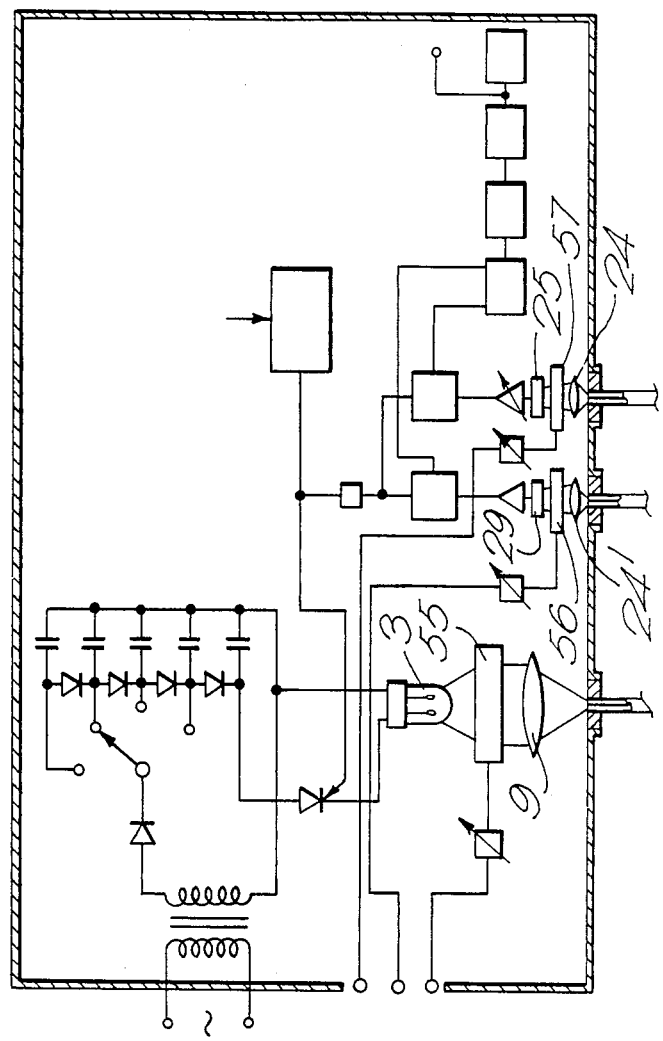

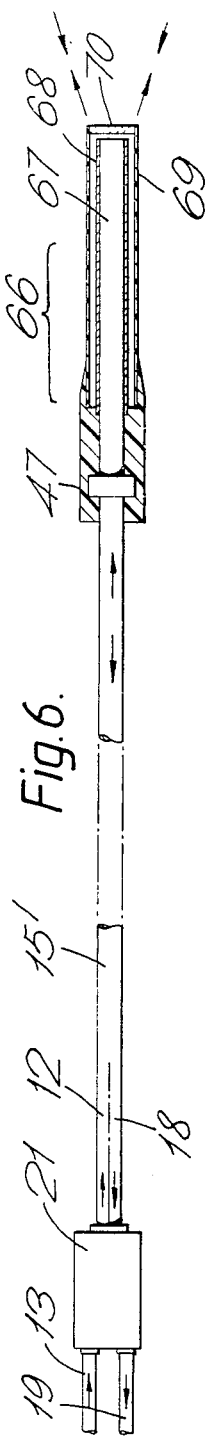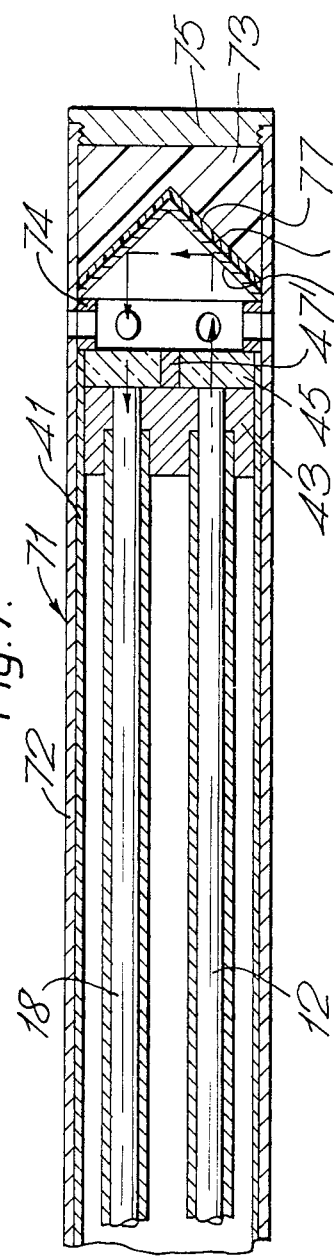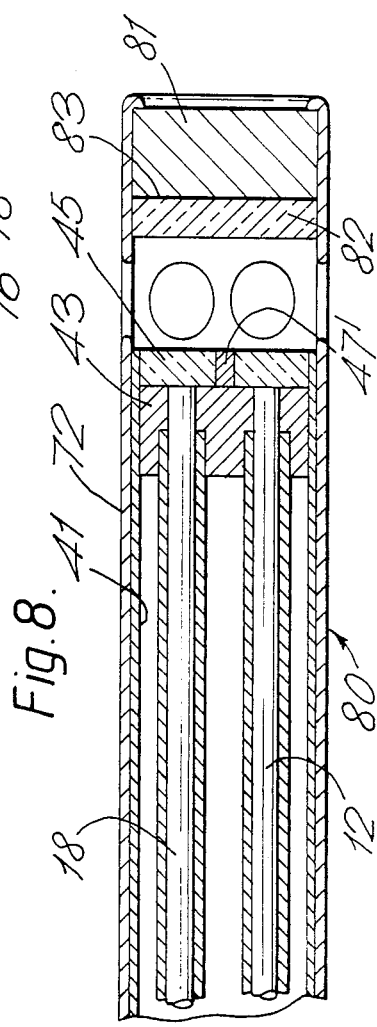

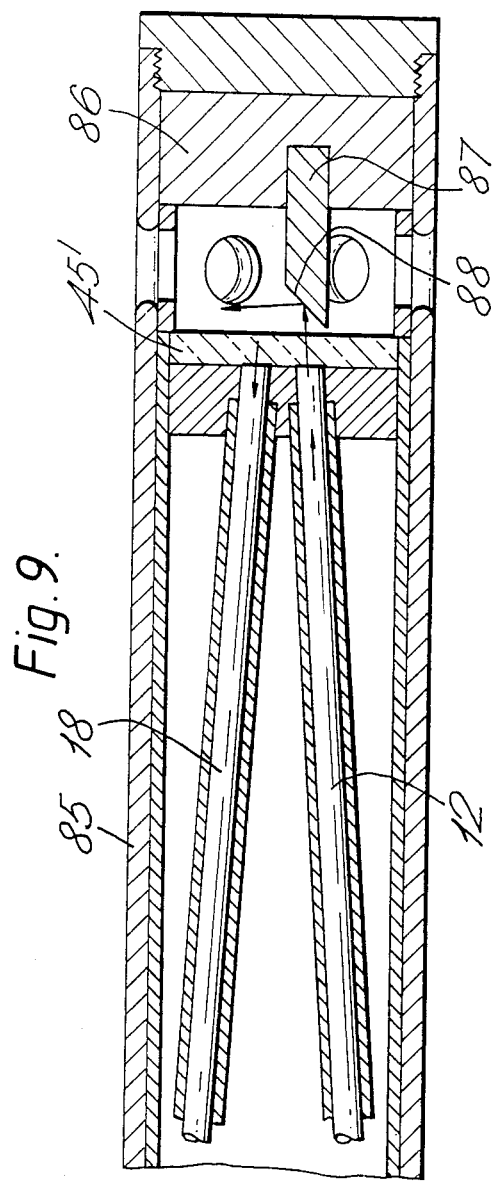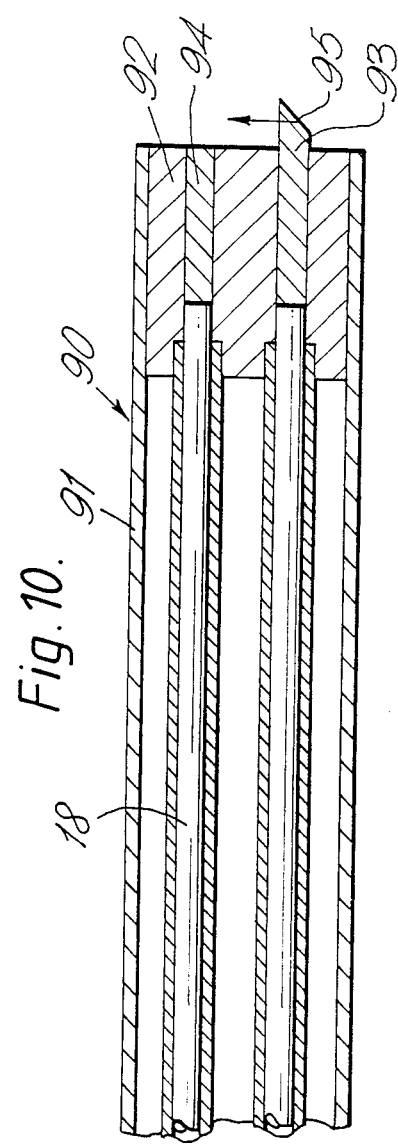

PRIOR ART FIXED TIME DELAY TRIGGER

ANALYTICAL OPTICAL INSTRUMENTS

This is a continuation-in-part application claiming priority to and connected with Ser. No. 293,895 filed Aug. 18, 1981, now abandoned, which in turn claims priority to British application No. 8027319 filed Aug. 21, 1980.

BACKGROUND OF THE INVENTION

The present invention concerns the measurement of optical properties of matter and in particular it relates to instruments which measure such properties as turbidity, absorption, reflection, fluorescence and phosphorence of a fluid sample or of a processed fluid, or which measure such properties (except turbidity) at a solid interface.

Instruments for the detection of these properties are well known but they have tended to be of a form suitable for use in a laboratory under specified conditions (to reduce ambient light disturbances). That is, instruments of the type of which the sample is taken to a test cell, or designed for specific industrial uses in situ. Designs are limited because of the difficulties involved in getting light to the point at which the test is carried out and in gathering the light resulting from the test operation in a prescribed precise manner for subsequent measurement. The advent of fiber-optics has ameliorated some of the problems of conveying light to and from a test site, but a single versatile system that has the performance of a highly specialized instrument and yet can be applied equally well to process control, on-site industrial measurement, in-vivo measurement, e.g. as a medical tool, or measurement under laboratory conditions has escaped the industry. Moreover, no single versatile instrument for use even under adverse lighting conditions and for inaccessible locations and/or adverse or hazardous environments, has become available.

The availability of such instruments has escaped the industry for many technical reasons. Primarily, the characteristics of flash light emission, electronic detector gating and fiber-optics combine to defeat the competitive accuracy of 1% which is achievable with conventional bulk sample spectraphotometers. Turning first to characteristics of light emission as, for example, with a Xenon flash tube, it is elementary understanding that the arc position within the tube varies with each flash. A tube element generally incorporates oppositely facing, parallel electrodes which permit the formation of an arc therebetween upon energizing. The specific relative location and therefore the amplitude and frequency of the arc during each flash cycle varies depending on where the arc strikes the electrode. Thus, the apex of the light cone emanating from the lamp randomly changes position with each flash which results in changes of the amplitude and frequency of emitted light. Consequently, these changes induce loss of specific repeatability and a corresponding diminution of detectability in a fixed detector system.

Detection of a large quantity of light passing through a bulky sample is not seriously affected by the foregoing consideration. However, the performance of a fiber optic-based detector is considerably impaired. Fiber-optics provide a target requiring a very specific geometry of light impingement in order to convey the light signal. Essentially, an optical fiber, conventionally having a diameter of 4 mm, has a limited cone of acceptance which must be substantially aligned with the source light cone in order to achieve sufficient detection. Bearing in mind restrictive optical characteristics of the optical fibers (refraction in "the light pipe"), it has been determined that the angle of the cone of acceptance is directly related to the light frequency. If light in the ultraviolet range is employed, the cone angle approaches 20° and if, visible, 50°. Accordingly, if the apices of the light cone and the cone of acceptance are not aligned within these ranges, the fiber will not "see" the light.

Where it is desired to couple a variable flash source such as a Xenon tube with a fiber-optic detector, the engineering and design must contemplate the limitations described above. Should they be ignored, the coupling back or return of the signal both in amplitude and spectral response, generated by the illuminated sample, is prevented or seriously impaired. Therefore, little or no detection is achieved.

Referring to a specific example of a Xenon flash tube in a spectrophotometer, Hutchins, U.S. Pat. No. 3,810,696, describes an instrument in which a flash is directed through a bulk sample containing cell where light transmission is detected by a dual photodetector. When employing the specific Xenon tube recited, by specification, light amplitude varies by no less than 10% and the incidence of the light flash ("timejitter" - cyclic repeatability) exceeds 200 nano seconds. No consideration is given to the use of a fiber-optic detector. Thus in addition to the foregoing problem, Hutchins, being representative of the prior art, fails to consider the requirement for alignment of the apices. Accordingly, unless alignment occurs by chance, no "light pipe" is enabled.

Taking into account the random placement of the arc, the limited cone of acceptance with fiber-optics, as well as the frequency relationship, the probability of achieving detection with a conventional device such as Hutchins, would be limited to minimal statistical chance —wholly unsatisfactory for purposes of reliable, repeatable measurement.

Adding to the foregoing problems, the art fails to properly account for the proportion of "real" light detected from the sample. Hutchins, exemplary of conventional systems, triggers or gates the detector only after light output attains a particular threshold. Generally, this threshold is based on either a particular fixed time after flash initiation or a fixed intensity of light transmitted. Combining fluctuations in source-light intensity and amplitude with this threshold concept of triggering, leads to a system which virtually defies repeatability. As a result of the proportionality of light detection based in pulse width and amplitude (which varies at minimum up to 10%) the prior art fails to achieve a system allowing for 1% detection accuracy. Especially when considering measurement of weak light signals from dilute samples, modification of a conventional detector such as Hutchins' would require considerations of source and detector optics alignment, as well as gating, neither being recognized.

SUMMARY OF THE INVENTION

The instant invention provides an analytical optical system which enables miniaturized construction and enhanced detection of low signal intensities in situ and even in the presence of considerable dark current (interference) and sunlight. The invention satisfies its purpose by recognizing the various above-described problems and interrelationship between the light source, optical fibers and gating sequencing.

In view of the foregoing, the long recognized need for a fiber-optic based optical instrument is evident. A system contemplating the problems and considerations set forth above, presents a unique solution heretofore not described. Accordingly, it is an object of this invention to provide such a system.

It is another object of this invention to present a workable fiber-optic based optical detection system which overcomes the foregoing problems.

Still another object of this invention is to provide an optical instrument capable of accurate, reproduceable measurements in a wide spectrum of applications.

Another object of this invention is to provide an optical instrument for in situ detection and measurement of dilute fluid systems.

It is a further object of the present invention to provide an optical probe of relatively small insertion cross-section having multiple optical channels.

Yet a further object of the present invention to provide a multi-channel optical probe of small insertion cross-section which specifically adapted to perform in situ one or other of the following optical tests: reflection, fluorescence reflection, transmission, absorption, fluorescence, phosphorescence or turbidity. These and other objects are satisfied by an optical instrument comprising a high intensity light pulse source, a first fiber-optic based channel means enabling light transmission to a selected site where the means and source are aligned to assure light transmission, the light enters the site and is returned by a second fiber-optic based channel means which leads to a measuring means for sensing and measuring the intensity of the light or selected portions thereof. The measuring means and source are controlled by a gating means for synchronous and coincidental gating thereof. Also, a storage means is employed to store the measured signal and to determine the ratio between the measured signal and the pulse intensity.

Pulsed light of high incident intensity so as to discriminate background illumination is conveyed to the site of the test by a probe. The probe is arranged adjacent to, or in intimate contact with, the matter under test, and by means of a first light-conducting fiber-optic cable connected between the probe and a light pulse generating means and the light resulting from the test operation is gathered by the probe or another probe in a prescribed direction relative to the direction in which the light is transmitted to the site and is conveyed therefrom to a detecting circuit for sensing with a first light sensing means by a second light-conducting fiber-optic cable, said first light sensing means being enabled to view the light collected by the probe or said other probe only during relatively brief periods coincident with the said pulses of light. The output of the first light sensing means is ratioed with the output of a second light sensing means enabled coincidentally with the first light sensing means and which receives light from the pulsed light source representative of the intensity thereof. Preferably the light received by the second light sensing means is collected at the site of the measurement by probe means and conveyed to the detecting circuit by a further fiber-optic cable, this light being representative also of the light incident upon the matter under test thereby removing from the measurement any short term effects due to obscuration of the incident light, for example at the probe window or in the first light-conducting fiber-optic cable. In turbidity measurements the second light-conducting fiber-optic cable gathers light which as been scattered whereas a third light-conducting fiber-optic cable gathers a sample of directly transmitted light.

With some measurements the spectral response is an important consideration. Accordingly, in one arrangement, means is incorporated to select the band widths of the excitation and/or collected light. Such means may include a laser as the light source. A laser may also be used as the light source particularly where transmission through optical fibers over long path lengths is necessary, for example with in-vivo measurements through a micro-diameter probe, e.g. one having a diameter of 3 millimeters.

In some measurements the angle of the collected light relative to the light incident upon the sample determines the form of measurement. It is sometimes necessary also to collect light from more than one direction. Precisely setting up the optical parts has therefore always caused difficulties and these difficulties are only partially overcome by the use of fiber-optic cables. The miniature prefabricated unitary probes provided by the invention, in conjunction with the use of a pulsed light source enables these problems to be completely circumvented even where measurements are required in hazardous environments or inaccessible positions. Accordingly, it is a further object of the invention to provide a unitary optical probe for use in the abovementioned measurements.

BRIEF DESCRIPTION OF THE DRAWINGS

Hereinafter the invention is described with reference to the accompanying drawings, wherein:

FIGS. 2 and 2A show the construction of the probe of FIG. 1 in greater detail;

FIG. 4 shows a modification of the system of FIG. 3;

FIGS. 6 to 10 show various forms of unitary dual channel optical probes constructed in accordance with the teaching of the invention.

DETAILED DESCRIPTION OF THE ILLUSTRATED EMBODIMENTS

Figure 1:
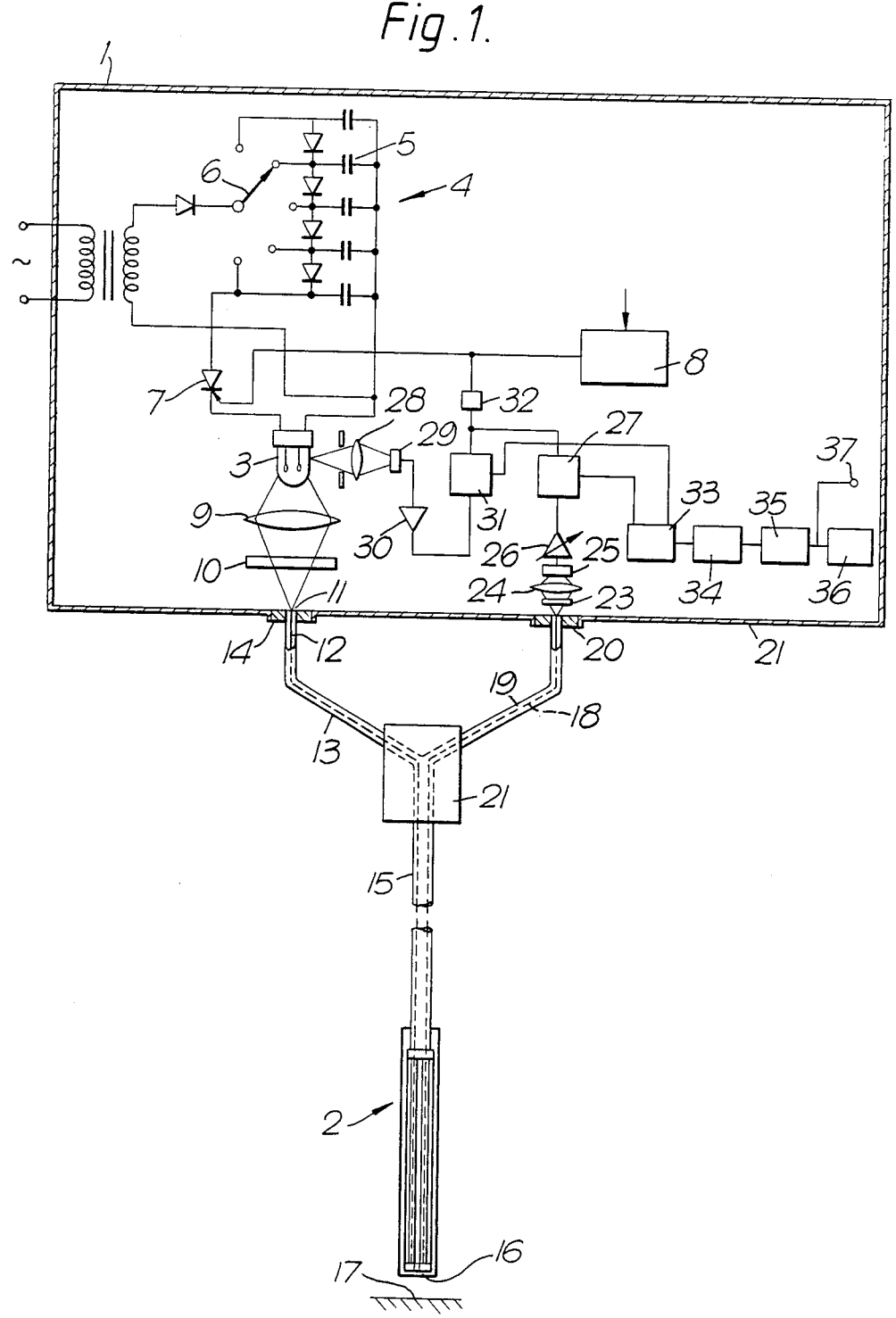
FIG. 1 shows a first optical measuring system according to the invention.

In FIG. 1, there is shown a basic form of the invention comprising a single beam analyzer 1 and a dual channel probe 2 arranged for measurement of fluorescence or phosphorescence at a fluid-solid interface.

Analyzer 1 comprises a light source 3, which may be a Xenon lamp or alternatively a laser, coupled to a conventional mains-operated drive circuit 4 containing a bank of capacitors 5 which may be selectively connected into the lamp discharge circuit by means of switch 6. The discharge of the capacitors through the lamp is controlled by silicon controlled rectifier 7 which receives enabling pulses from a control circuit 8 at a rate which may be set at the analyzer, or by some external source; e.g., control circuit 8 may be triggered by an external source to provide single enabling pulses in synchronism with some external event. For most applications the control circuit is set to provide enabling pulses at a repetition rate of between 1 and 100 per second.

The light from the lamp 3 is collected by a lens system 9 and directed via a first light modifying means 10 into the first end 11 of a first bundle 12 of light conducting optical fibers contained in a flexible cable 13 arranged at a location defined by an adaptor 14. For the application described, the first light modifying means comprises a simple optical filter which suppresses all light having wavelengths corresponding to the wavelengths of the anticipated fluorescence or phosphorescence and longer wavelengths.

The bundle 12 of light-conducting optical fibers comprise a set of continuous fibers which extend without break through cable 13 and a further flexible cable 15 to the tip 16 of the probe 2 arranged adjacent to and spaced closely from the interface 17 being measured. Various diameters and numbers of fibers in the bundle are used according to the nature of the test and the diameter of probe which can be used having regard to the accessibility of the said interface. In a typical application there are at least 30 fibers in the bundle and the bundle has a diameter not exceeding one millimeter. A similar bundle 18 of optical fibers extends from the tip 16 of the probe 2 parallelly therealong and via cable 15 and further flexible cable 19 to a location defined by an adaptor 20 at the analyzer 1. Cables 13 and 19 merge into cable 15 at junction member 21.

Each of the adaptors 14 and 20 comprises an optical plug and socket of a standard type known in the art, the plug part being connected to the end of the respective cable 13, 19 and arranged axially with the respective optical fiber bundle and the socket part being mounted on the analyzer casing 21 and receiving the plug part with minimum clearance. Fastening means is provided to secure the plug part within the socket part and prevent accidental disconnection.

Fluorescent or phosphorescent light emitted at the interface under examination and impinging on the tip of the probe opposite the second bundle of optical fibers enters therein and is transmitted to the adaptor 20. Upon emerging from the fibers, this light passes through a second light modifying member 23 and is collected by lens system 24 and focussed onto a first light detecting cell 25. An amplifier 26 of adjustable gain couples the signal from the cell 25 to a first sampling circuit 27. Second light modifying means 23 is similar to the first light modifying means in that it comprises, for this application, a simple optical filter; this filter, however, is chosen to suppress light having wavelengths shorter than the wavelengths of the fluorescent or phosphorescent light.

A third lens system 28 gathers light emitted by the lamp 3 and focuses it onto a second light detecting cell 29. A fixed gain amplifier 30 couples the output signal from the second light detecting cell 29 to a second sampling circuit 31. Sampling circuits 27, 31 each receive an enabling signal from a circuit 32 connected to the output of control circuit 8. Circuit 32 controls the sampling circuits 27, 31 so that they sample the outputs of the respective amplifiers coincidentally and synchronously with the pulse of light emitted by the lamp and only for the duration of the pulse of light. A more detailed explanation of this factor is described below.

An electronic ratio-determining circuit 33 receives an input from each of the sampling circuits 27, 31 representative of the light impinging upon the respective detecting cell during the immediately precedingly occurring pulse of light and provides at its output a signal representing the ratio of the signals provided by the said detecting cells. This output signal is fed through a characterizing circuit 34 and a smoothing circuit 35 to a digital display meter 36 and to an output terminal 37.

In FIG. 2 there is shown in greater detail the construction of probe 2. A plastic fitting 40 at the end of the probe furthest from the tip leads the fiber bundles 12, 18 into respective chromium-nickel alloy tubes 41, 42 each no more than 1.5 millimeters outside diameter each extending substantially over the length of the probe. At the far end of the probe these tubes enter a stainless steel plug 43, the main purpose of which is to provide a precise location of the fiber bundles. This plug is swaged into an outer stainless steel sheath 44 which receives the plastic fitting 40 at its other end. A specially constructed silica window 45 is fused onto the end of the outer stainless steel sheath 44 and the latter is totally encased in a flat ended transparent silica tube 46. A plastic sheath 47 is bonded onto the flexible cable 15 at one end and passes over the open end of the silica tube at its other end, thereby joining the probe to the flexible cable 15 and forming a hermetic seal at this position to prevent the ingress of contaminants. Silica window 45 is formed with an optical channel divider 47A comprising a black opaque glass insert extending through the depth of the window. As shown in FIG. 2A it is arranged to run in the mid plane between the two bundles of fibers and is constructed to prevent light leaving the fiber bundle 12 from being substantially reflected into the other fiber bundle 18, for example by the inner and outer surfaces of the silica tube 46 at the tip of the probe.

The device illustrated in FIGS. 1 and 2 operates in the following manner. Control circuit 8 produces controlled pulses which are used to gate on SCR 7 and circuit 32 which in turn switches each of the sampling circuits 27 and 31 to a sampling mode. Capacitor bank 5 discharges through the lamp 3 causing a flash or pulse of light to be emitted therefrom. The intensity of this flash is adjusted by setting switch 6 so as to prevent saturation of the light cell 25 for a standardized test. At the end of the flash, circuit 32 disables the two sampling circuits 27, 31 which automatically enter into a hold mode in which their output signals are representative of the signals provided by detectors 25 and 29 during the immediately preceding flash. Light which enters the fiber bundle 12, having traversed the lens system 9 and the filter 10, is transmitted with relatively low loss to the probe tip where it emerges into the fluid immediately surrounding the probe and impinges on the immediately facing surface undergoing examination. This light contains only wavelengths shorter than the fluorescing (or phosphoresing) light by virtue of the action of the filter comprising the light modifying means 10. Critical geometry is used to substantially reduce the stimulating light, reflected at the interface, from entering the fiber bundle 18 through the window 45, i.e. the probe is accurately spaced by some physical means so as to be a precise distance from the interface, thereby ensuring a maximum cone angle for the gathered light whilst still ensuring that the tip of the fiber bundle 18 remains in shadow with respect to any reflected light by reason of the optical channel divider. If desirable, physical spacing means may be employed to secure the proper positioning.

The light entering the fiber bundle 18 is transmitted to the light modifying means 23 where any remaining light of wavelengths corresponding to the stimulating light is removed by filtering. The filtered light is gathered by lens system 24 and focussed onto light cell 25, which may be of any of the conventional forms in present use, dependent upon the wavelengths of light being employed for the measurement, including photo diodes and photo multipliers. The gain and threshold of amplifier 26 are adjusted to eliminate the dark current signal (i.e. a signal when there is no flash occurring) and to provide an appropriately scaled output signal which is ratioed with a signal from the lamp 3 in ratio-determining circuit 33.

Characterizing circuit 34 will usually have a linear transfer characteristic; but other transfer characteristics, e.g. logarithmic, may be preferred for some applications.

The level of intensity of the fluorescent or phosphorescent light resulting from the stimulating light is directly proportional to the intensity of the stimulating light and it follows that any variation in the latter will cause a proportionate change in the signal provided by the light cell 25. However, a similar proportionate change occurs in the output of the light cell 29 and these variations cancel in the ratio-determining circuit 33 with the consequence that the instrument is insensitive to the absolute level of intensity of the light source. For the same reason, the instrument is also insensitive to aging effects in the light source and normal variations in the voltage of the power supply. Because of the high intensity of illumination, the level of background lighting or any variation in intensity thereof is of no consequence during the occurrence of the flash of light, and as the detecting channels are only gated on during this period there is no averaging effect due to background illumination. Despite the extremely high intensity of illumination, the average power dissipation is around 5 watts and any heating effect at the site of the measurement can be completely disregarded.

The instrument described hereinbefore is adaptable to multi-channel use in which there is a plurality of optical inputs, each having a respective optical adaptor and each being served by a respective optical cable connecting the input to a respective probe or, alternatively, to a unitary multi-channel probe. One such form is illustrated diagrammatically in FIG. 3 in which the analyzer differs from the arrangement of FIG. 1 only in that the components forming the reference signal channel which monitor the lamp output, are physically rearranged to receive an optical input from the fiber bundle 54 in a cable 50 connected to a third optical adaptor 51. The analyzer of FIG. 3 can be given the capacity to perform as the analyzer of FIG. 1 simply by duplicating the optical components of the reference signal channel and arranging for the input of amplifier 30 to be switchable from the light cell monitoring the lamp output to a light cell arranged coaxially with the third optical adaptor 51. Like components in FIG. 3 have the same references as the components of FIG. 1.

Figure 3:
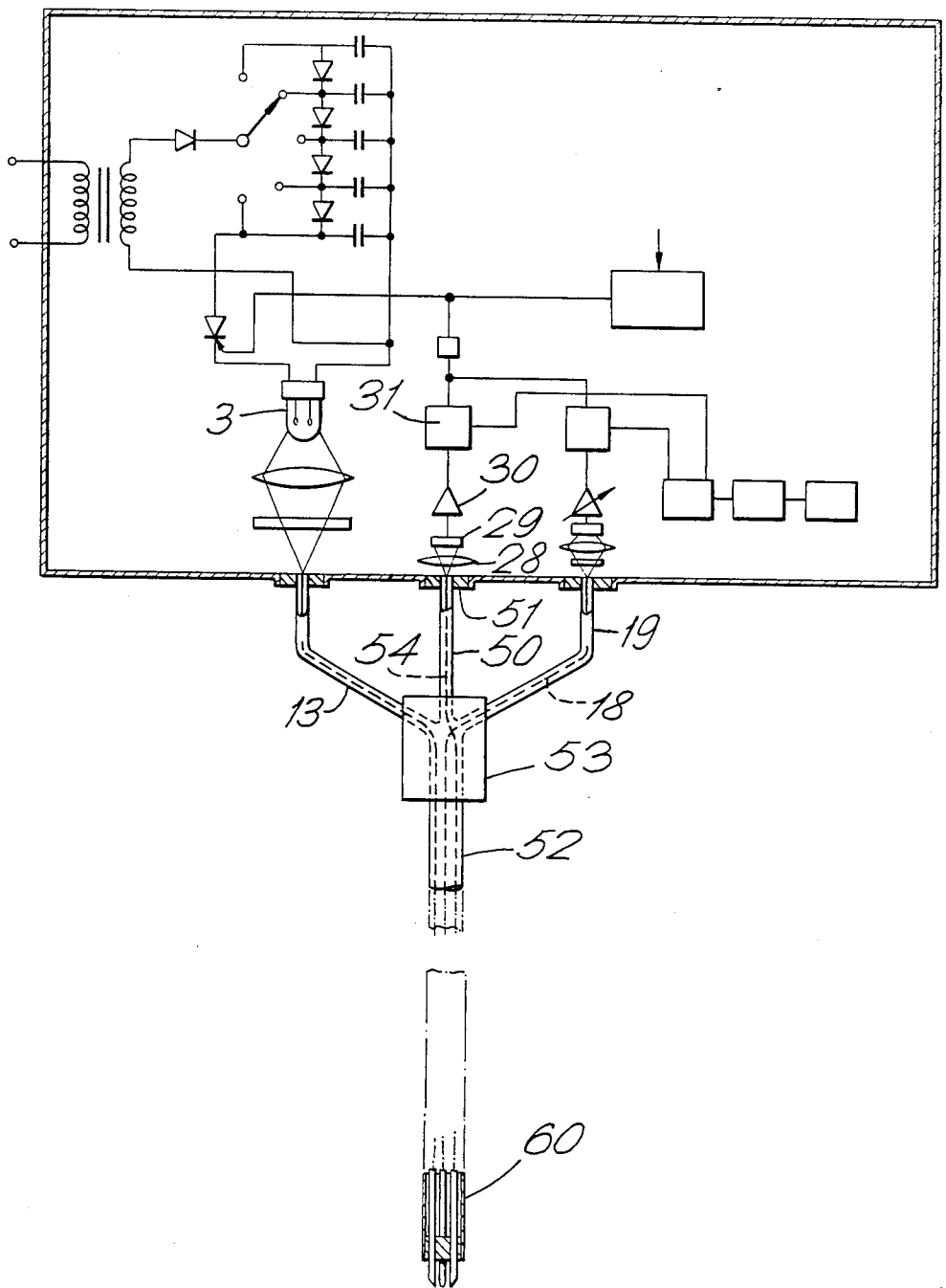
FIG. 3 shows a second optical measuring system according to the invention.

FIG. 3 shows the analyzer in use with a three channel probe 60, the construction and purpose of which is dealt with more fully later in this description in relation to FIG. 5. In general terms, however, the provision of a third channel in the probe allows a reference optical signal to be gathered at the site of the measurement rather than at the light source 3 and therefore enables disturbances due to obscuration of the transmitting light channel to be circumvented. The third channel is usually arranged to receive light transmitted directly through the fluid under test. This arrangement is particularly useful where the cable lengths are considerable because the measuring site is inaccessible or in a dangerous environment, and the signals at the light cells 25 and 29 become attenuated as a consequence.

Conveniently all three cables 13, 19 and 50 are merged into a single flexible cable 52 by means of the junction block 53.

A modification of the analyzer of FIG. 3 is shown in FIG. 4. This differs only in that remotely adjustable monochromators (55, 56 and 57) are incorporated in each of the transmitting and two receiving channels between the light source 3 and the collecting lens 9 and between the collecting lenses (24, 24') and the respective light cells 25, 29. These serve in place of the previously described filters. The monochromators can be linked up with a computer program to allow a computer to carry out automatically a complex sequence of tests for continuous or batch processing. For example a large number of tests can be carried out sequentially and repetitively on a plurality of samples and the results automatically monitored for change and/or logged. Alternatively the monochromators can be replaced by simpler hand-operated models and the tests carried out manually. Similar modifications with respect to the use of monochromators can be carried out on the analyzer of FIG. 1.

Hereinafter various probes are described which may be used with the analyzers illustrated in FIGS. 1, 3 or 4, depending upon their analytical function and the number of optical channels in the probe. In particular, they depend for their design on the property which specific materials or substances have to differentially deflect, reflect, absorb and re-emit light in dependence upon the wavelength of light used and detected. For this reason the materials used for the optical fibers, the windows at the end of the probe, light-conducting rods, mirrors and reflecting surfaces are chosen to suit the wavelengths of light used and the looked-for spectral responses. In general the light-conducting materials will be formed from either glass or silica and the reflecting surfaces will be provided by a deposited coating either of aluminum-silica dioxide or a protected dielectric. The production of such materials and coatings are already known in the art and will not be described further herein.

Figure 5:
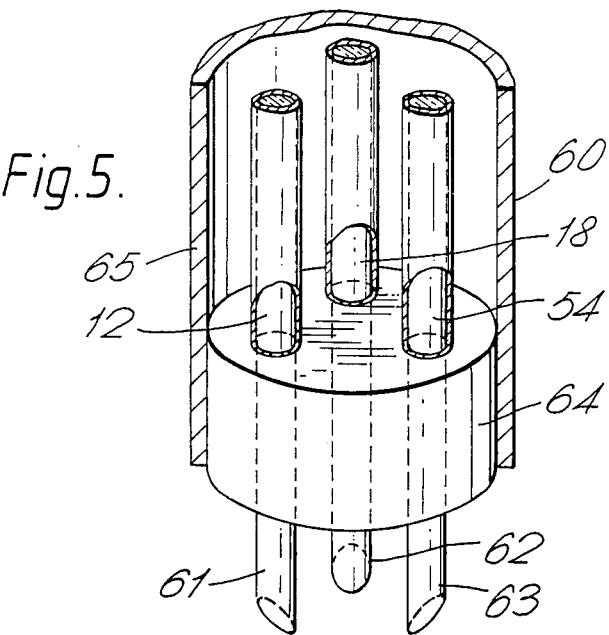
FIG. 5 shows a detail of the construction of the probe illustrated in FIG. 3.

FIG. 5 shows in greater detail the measuring end of the probe 60 illustrated in FIG. 3. This has three glass or silica rods 61, 62, 63 which are aligned within a stainless steel plug 64 at the end of the probe coaxially with respective bundles of light-conducting optical fibers 12, 18 and 54 corresponding to the transmitting cable 13 and the two light detecting cables 19 and 50. Each rod projects into the fluid under test and is finished with a 45° chamfer, the surface of which is provided with a reflecting layer. The rod 61, corresponding to the transmitting cable, and the rod 63, corresponding to the reference signal cable 50, are aligned so that light in the rod 63 is the light which has passed directly in a straight line between the rods 61 and 63 having been bent through two right angles by the respective reflecting 45° surfaces. The signal provided at the cell 29 therefore contains a factor corresponding to the light absorption by the fluid under test. During the passage of light between the rods 61 and 63 some light is scattered, and a proportion of the light which is scattered laterally at a right angle enters the rod 62 and is reflected by the reflecting layer on the chamfered surface into the fiber bundle 18. This proportion is detected by the light cell 25. Therefore, the ratio of scattered light to transmitted light which expresses the turbidity of the fluid under test, is formed in the ratio-determining circuit 33.

Plug 64 is entered into a stainless steel tube 65 which forms a rigid protective sheath for the probe. A seal between the plug 64 and the tube 65 may be formed by any convenient means, e.g. welding, or pressure between a threaded ring and a polytetrafluoroethylene sealing ring (not shown).

The probe 66 shown in FIG. 6 is a dual channel probe intended for use with the analyzer of FIG. 1 in the measurement of reflection and fluorescent reflection, particularly at a fluid-solid interface. The two sets of fibers in bundles 12 and 18 are intimately mixed within cable 15' so that a single bundle of fibers 67 enters the probe 66 and is contained by a single rigid stainless steel tube 68. A silica sheath (69) having a flat optical window 70 covers the stainless steel tube and is sealed at its open end by the plastic sheath 47.

In use, because of the mixing of the fibers, light is both emitted and received at all points across the window 70. Some emitted light (i.e. light from the bundle 12) is reflected at the surfaces of the window and some light is scattered in the sample and finds its way back into the fibers of bundle 18. For reasonable accuracy these effects must be offset during reflection measurements per se, but the use of filters provides rejection of the reflected light during measurements of fluorescence.

In FIG. 7 there is shown the measurement end of a probe 71 intended for the measurement of absorption in fluids. The probe is encased in a stainless steel tube 72, instead of a silica sheath, but apart from this change and also the construction of the tip it is otherwise similar to the probe illustrated in FIG. 2 and has the same optical window 45 with its black glass insert 47. Tube 71 extends beyond the window 45 and contains also metal plug 73 which is positioned by means of a perforated collar 74 and a screw cap 75 which is located at the end of tube 71. Metal plug 75 contains an accurately aligned 90° angle V groove 76 which may, for example be pressed into a soft metal blank from which plug 73 is formed. Very accurate optical surfaces are provided on the walls of the V groove by lowering into the groove a tool having a complementary formation on its end which has been very accurately finished, and by casting a plastics substrate 77 between this tool and the plug 73. A dielectric reflecting surface 78 is then deposited upon the surface of the substrate material exposed by the withdrawal of the aforesaid tool. These reflecting surfaces act in the same way as a corner-cube prism in returning light emitted from the fiber bundle 12 to the fiber bundle 18. The light detected at the light cell 25 contains a factor proportional to the absorption of light in its passage from the fiber bundle 12 to fiber bundle 18. Since the path length is fixed by the construction of the probe, this factor can be determined by standardizing the instrument to a known sample. Fluid is admitted to the space between window 45 and the plug 73 by providing perforations in the tube 72 which align with the aforesaid perforations in the collar 74.

The probe 80 illustrated in FIG. 8 is of basically the same construction as the probe 71 shown in FIG. 7 and has a similar purpose, but in place of plug 73 there is a plug 81 swaged in tube 72 on which a mirror 82 is mounted. The latter is sealed onto the wall of the tube 72 by means of an impermeable adhesive to prevent the penetration of corrosive fluids to its underside where a reflective coating 83 of aluminum-silicon dioxide is deposited. The design is cheaper than that of FIG. 7 but a smaller proportion of light will enter the fiber bundle 18. It is therefore less suited to a long probe design in which light attenuation becomes a significant factor.

FIG. 9 shows another probe 85 of similar construction to that of FIG. 7 but is intended for the measurement of fluorescence occurring in a fluid. So as to maximize the returning signal the fiber bundles 12 and 18 are brought almost into contact where they end within the probe and a plain window 45' is provided so as to prevent ingress of fluid into the probe but for no other purpose. In place of plug 73 there is plug 86 containing a silica rod 87 aligned accurately with the end of fiber bundle 12. Rod 87 has a 45° chamfer 88 on an end extending almost into contact with window 45'. A dielectric reflecting layer is provided on the chamfered surface. Light leaving the fiber bundle 12 is reflected across the face of the window 45° and causes fluorescence to occur within the fluid in the immediate vicinity of the chamfered surface. A proportion of the fluorescence which occurs at right angles to the general direction of light reflected by the chamfered surface enters the fiber bundle 18 and is representative of the stimulated fluorescence.

Probe 85 is the preferred design where the depth of penetration of the probe within the fluid under test presents no problems. An alternative probe 90 giving less efficient results but intended where little or no penetration of the probe into the fluid is possible, is shown in FIG. 10. Probe 90 has an outer stainless steel sheath and is fitted with a plug 92 into which is set a pair of spaced-apart silica rods 93, 94. Rod 93 extends beyond the end of the probe to a 45° chamfered end 95. A dielectric reflecting surface is deposited upon this chamfered surface and the rod is aligned so that light leaving it is directed across the corresponding end of rod 94 which is terminated flush with the end of the probe. Only scattered light or fluorescent light is able to enter the rod 94. At their inner ends rods 93 and 94 are respectively aligned within plug 92 with the fiber bundles 12 and 18.

Figure 11:
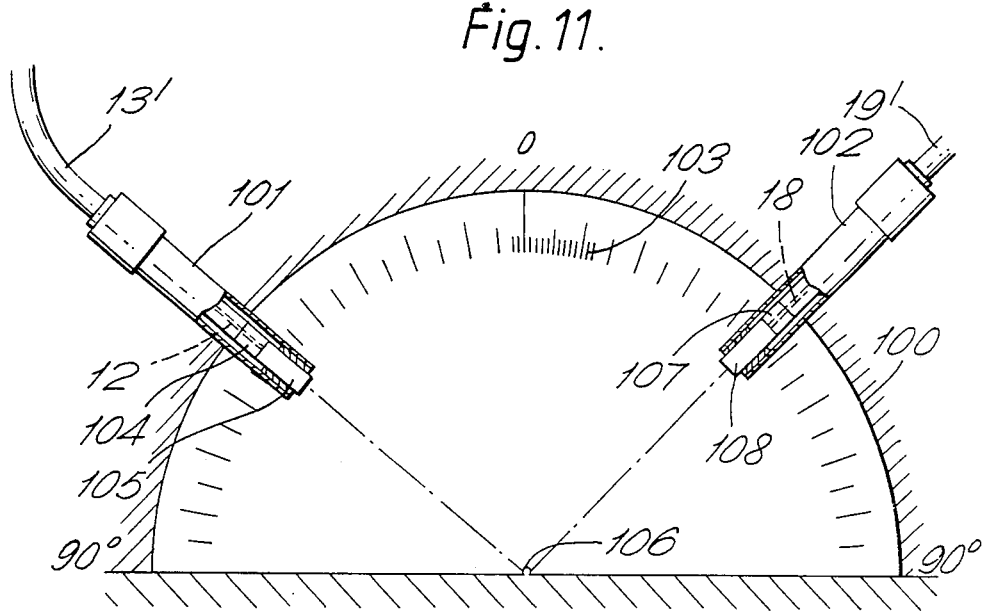
FIG. 11 shows an arrangement for measuring optical reflections at a fluid-solid interface.

The arrangement of FIG. 11 which is intended for examination and measuring spectral reflections at a fluid solid interface comprises a pair of single-channel probes 101, 102 respectively connected to optical cables 13' and 19' and supported above the testing site by a holder or jig 100. One or both the probes may be moved in concentric circular arcs over the measurement site and, suitably, a protractor scale 103 is provided so that the angular positions of the probes can be instantly seen. Probe 101 contains fiber bundle 12 the end of which terminates concentrically within plug 104 a short distance from the end of the probe. A lens system 105 collects the light leaving the fiber bundle 12 and focusses it substantially at the center of curvature 106 of the circular arcs. The fiber bundle 18 similarly ends concentrically within a plug 107 a short distance from the end of probe 102. A lens system 108 collects light reflected from the interface at the aforesaid center of curvature and directs it into the fiber bundle 18. If desired, a third probe (not shown) containing fiber bundle 54 and coupled to a cable terminating in adaptor 51 may be provided so that measurements of the ratio of spectral reflection to ordinary reflection may be determined.

As indicated above concerning the discussion relating to the coincidental and synchronous circuit actuation, the gating of the instant invention contemplates a mark/space ratio on the order of 1:22,000.

Figure 12:
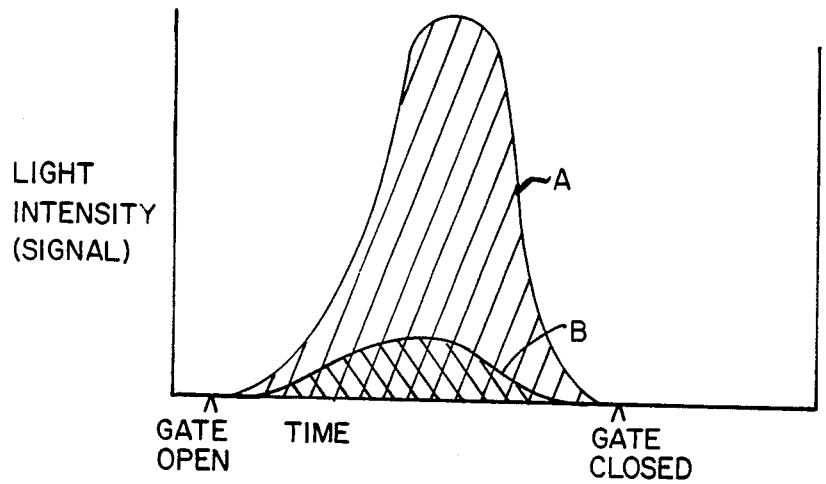
FIG. 12 is a graphic representation of curve of light intensity plotted against time of the source and detected light of the instant invention.
Figure 13:
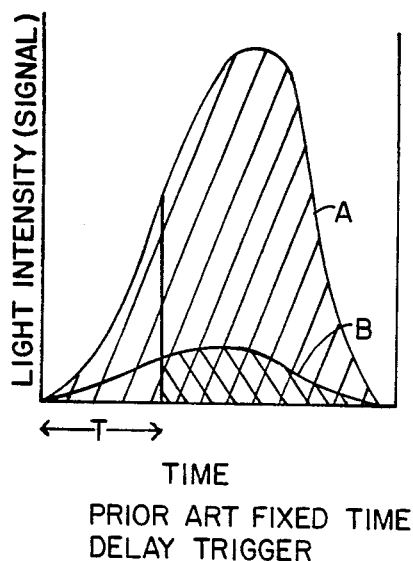
FIG. 13 is a graphic representation of a curve similar to that of FIG. 12 but for a fixed time trigger delay.
Figure 14:
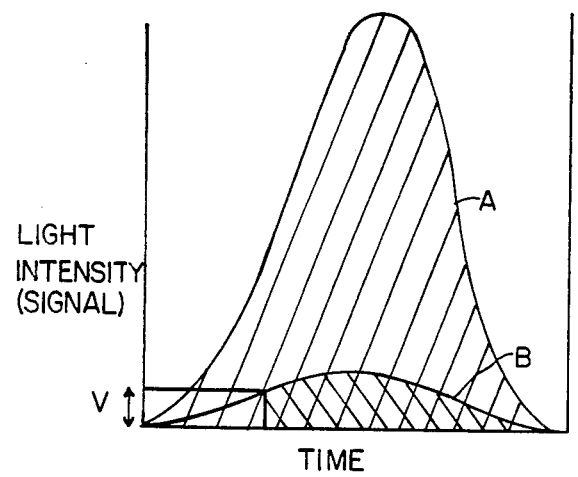
FIG. 14 is a graphic representation of a curve similar to that of FIG. 12 but for a constant amplitude trigger delay.

In specific reference to the effect of synchronous gating generally described as it relates to control circuit 8, SCR 7 circuit 32 and sample circuits 27 and 31, FIGS. 12–14 illustrate a critical advantage of the instant invention over conventional systems or combinations thereof. As noted control circuit 8 coincidentally and synchronously actuates the light flash and sample circuitry. This provision enables the instant invention to see the entire flash rather than certain portions thereof.

In FIG. 12 this becomes apparent where curve A represents the entire light flash intensity between the time of discharge of capacitor bank 5 and dissipation. During the entire duration of the light flash, sample circuits 27 and 31 are gated open thereby permitting the sample emitted light intensity (represented by curve B) to be determined. The curve differs considerably from those illustrated in FIGS. 13 and 14, which respectively illustrate conventional fued time trigger delay (represented by t) and constant amplitude triggering (represented by amplitude v). Neither of these conventional triggers permit the entire sample emission signal to be detected.

The principles underlying the conventional fixed time or threshold intensity devices are elementary wherefore it is not believed that further explanation is necessary for the purpose of this disclosure. Suffice it to underscore that both of the prior art methods clip (cut off) the first portion of the pulse. As noted above, due to the variation of pulse amplitude and intensity due to the flash lamp characteristics and the fiber-optic channels, the trigger thresholds also vary. Thus, either of the foregoing prior art methods fail to enable repeatable sample and hold start points and, consequently, detection and measurement.

The synchronous and coincidental gating of the instant invention, however, does facilitate precise repeatable measurement from pulse event to pulse event, even at the time intervals of 1–50 microseconds, which are contemplated herein. Moreover, measurements herein account for both the optical signal from the pulsed lamp and any background signal (ambient light and dark current) interference. As signals from interference may very well attain the same level magnitude as that from lamp pulse, the gating allows the instant invention to discriminate therebetween and measure both accurately. Lastly, where the mark-space ratio between gate open and gate closed is in the order of 1:22,000, as contemplated herein, the interference signals are correspondently reduced. Thus, only the very low "real" signal intensities generated from the sample are measured.

Hereinbefore various arrangements of analyzers and associated pulsed-light optical probes containing the inventive concepts have been described. Various alternative arrangements and modifications of these analyzers and probes will occur to skilled workers in the art of optical measurement. All such variations and modifications are considered to be within the ambit of the invention which is limited only by the scope of the appendant claims.

We claim:

1. In a field instrument for pulse-light one-shot or cyclic in situ on-site measurement of such optical properties of a sunlight exposed fluid or of a fluid solid interface exposed to sunlight as reflection, flourescence, phosphorexcence, absorption and turbidity, the improvement comprising the combination of:

electronically gated light source means for producing light pulses emitted at a prescribed repetition rate up to approximately 100 Hz, said source means including (a) a triggerable light source having the characteristics of a Xenon flash lamp which, when triggered, provides a brief pulse of light of extremely high intensity, and (b) control means for providing triggering pulses for operation of said light source;

multi-channel single probe means comprising an elongated tubular member containing two or more light channels including first channel means comprising first light-conducting fiber means for conveying each said pulse of light to a specific point in the said fluid at the site and a first light-conducting fiber-optic cable for conducting said pulses to said first light-conducting fiber means, said fiber-optic cable being so aligned with respect to said light source to provide an efficient light pipe;

second returned light channel means, comprising second light-conducting fiber means for collecting light emitted from a prescribed direction at said point being positioned to provide a maximum cone angle at the interface of the surface for receiving the emitted light collected by the second light-conducting fiber means and being shielded to remain in shadow relative to reflected light and a second light-conducting fiber-optic cable for conveying the light responding in said direction to said pulses;

means for measuring the light conveyed to the site and for measuring at least a prescribed portion of the light from the site along said second channel means;

sampling means for receiving (a) signals corresponding to light intensity conveyed to the site and (b) signals corresponding to said measurements of light from the site;

gated electronic means including a disabling circuit coupled to said sampling means and responsive to said triggering pulses for enabling said measuring means only prior to and during said brief occurence of said pulse of light, said measuring means including means for sensing the intensity of the pulse of light conveyed to the site and means for sensing the intensity of light returned from the site through said second light-conducting fiber-optic cable where said disabling circuit disables said measuring means after said pulse; and means for storing the aforesaid signals representing light intensity, said storing means being updated on the occurrence of each pulse.

2. In a field instrument according to claim 1 wherein the said light source comprises a Xenon lamp, charge storage means, and a controlled solid state diode connected in series.

3. In a field instrument according to claim 1 wherein the control means comprises a one-shot device having an input for receiving external control signals.

4. In a field instrument according to claim 1 wherein the control means includes means for enabling selectable operation at a repetition rate which is selectable between zero and in the order of 100 cycles.

5. A field instrument according to claim 1 further comprising a plurality of probe assemblies, each probe assembly having at least two light channels including the respective fiber-optic cables, each said cable being connected to a standardized plug, said instrument including corresponding socket means into which said plug fits so as to permit said any one probe assembly to be selectively insertable into the system to convey light to and from the site of interest, respectively.

6. In a field instrument according to claim 1 wherein said multi-channel single probe means includes a third returned-light means comprising a third light-conducting fiber means adapted to collect a sample of the light transmitted to the said point and a third light fiber-optic cable, and wherein said third returned-light channel means includes means for measuring said sample of light.

7. In a field instrument according to claim 6 wherein one of said third returned-light measuring channel means returns a portion of light in said pulse which has been directly transmitted through the fluid at said site, and said light is made the input to the sensing means for determining the intensity of the light pulse conveyed to the site.

8. In a field instrument according to claim 6 further comprising light modifying means arranged in the path of the light pulse conveyed to the site and in one or more of the returned-light channels.

9. In a field instrument according to claim 6 wherein the light modifying means comprise adjustable monochromators.

10. In an instrument according to claim 1 where said measuring means includes a photo multiplier.

11. In an instrument according to claim 1 where gated electronic means can achieve a mark space ration of 1:22,000.

12. A system for measuring properties of a fluid substance on site and in situ, the system comprising:
a light source having the characteristics of a Xenon flash tube which is triggerable to generate a flash pulse of light of high intensity over a broad spectrum of wavelengths;
triggering means coupled to said light source to provide a trigger input thereto, said triggering means having a gate input and a signal input;
cell-less single probe optical detecting means comprising first fiber-optic channel means for guiding pulsed light emanating from said light source down said probe toward a specific point of interest in the fluid;
second fiber-optic channel means for collecting pulses of light emitted by the fluid at the said point of interest in response to the said light pulses transmitted thereto, said second fiber-optic channel means being positioned within said probe in a manner to provide a maximum light cone angle thereby maximizing light collecting efficiency and being positioned to minimize interference from reflected light;
measuring means for (a) sensing the intensity of light conveyed to said point of interest at the site by said light source and (b) sensing the intersity of light travelling from said point of interest along said second channel means, said measuring means having an enable input;
means, coupled to receive input from said measuring means, for storing one signal representing the sensed intensity of light conveyed to the site and another signal representing the sensed intensity of light travelling from the site along said second channel means;
control means for coincidentally and synchronously selectively providing a gate pulse to said gate input of said triggering means and said measuring means said control means further including a disabling means to disable said measuring means;
means for combining said one signal and said other signal to provide a measurement of an optical property of the sample substance; and
wherein said control means is connected to the gate input of said triggering means and to the enable input of said measuring means and wherein gate pulses from said control means cause said triggering means to trigger said light source and said measuring means is enabled for substantially only the duration of each gate pulse.

13. A system for measuring properties according to claim 12 wherein said control means comprises a commandable one-shot device which, upon each single input command, conveys only one pulse of light from said light source to the site of interest; and
wherein said cell-less, single probe optical detecting means further comprises:
a plurality of returned-light fiber-optic channels along which light from the site of interest can travel enroute to said measuring means, one of said returned-light channels along which light from the site of interest travels being said second fiber-optic channel means; and
means for selectively varying the level of signal flowing through said triggering means when gated, said varying means being coupled to the signal input of said triggering means.

14. A system for measuring properties according to claim 13 wherein each returned-light fiber-optic channel includes means for passing only a predefined band of wavelength;
the system thereby being able to make measurements for a plurality of bands of wavelengths with a single light source.

15. A system for measuring properties according to claim 14 wherein each returned-light fiber-optic channel is oriented at a prescribed angle relative to the site of interest.

16. A system for measuring properties according to claim 15 wherein said triggering means includes a silicon-controlled rectifier and wherein the measuring means includes at least one photomultiplier which senses light intensity.

17. In a system according to claim 12 where said measuring means includes a photo multiplier.

18. In a system according to claim 12 where said control means can achieve a mark space ratio of 1:22,000.

19. An optical instrument for measuring optical properties of a fluid at a prescribed site, comprising:
(a) a light source for emitting a high intensity light pulse of predetermined duration,
(b) first channel means for conveying said light pulses to the site, said first channel means comprising a first light-conducting probe and a first optical fiber where said optical fiber and light source are so aligned to enable light transmission therebetween, (c) second channel means for conveying light returning from the site, said second means comprising a second light-conducting probe and a second optical fiber, said second light conducting probe being positioned to provide a maximum cone angle to maximize collection from the site of light emitted by said first light conducting probe while minimizing the collection of ambient light and said first and second light conducting probe are in close proximity to each other, (d) first measuring means for sensing and measuring the intensity of light or selected portion thereof returned from the site through said second channel means, said measuring means generating a first signal corresponding to said light intensity, (e) second measuring means for measuring the gating control means for enabling said first measuring means during the entire occurrence of the light pulse, said control means being electrically connected to said light source and said first measuring means for synchronous and coincidental gating, (f) third measuring means for measuring the intensity of the light pulse from said light source and generating a second signal corresponding to said light pulse intensity, (g) storage means for storing said signal, and (h) means for providing a ratio between said first and second signals.

20. An optical instrument according to claim 19 wherein each channel means comprises a plurality of optical fibers and the second channel means is aligned substantially in the same direction in which the first channel means transmits said pulse into the fluid.

21. An optical instrument according to claim 19 further comprising a tubular housing for securing said first and second channel means as a probe, the cylindrical wall of said housing extending beyond the probe and is perforated to provide an enclosed space which is accessible to the fluid under test, said housing containing reflecting means spaced apart from but facing the end of the probe and said first and second channels each terminating in a plane perpendicular to the longitudinal direction of the probe and wherein light is transmitted from the first channel into said enclosed space generally in a first direction parallel to the longitudinal axis of the probe towards said reflecting means and after reflection is transmitted in a direction generally 180° displaced from said first direction into the said second channel.

22. An optical instrument according to claim 19 further comprising a tubular housing for securing said first and second channel means as a probe wherein said first channel is terminated in a light-conducting rod which has a light-transmitting end which projects sufficiently into the space beyond the probe to allow the exposed end to be given a 45° chamfer, and wherein said chamfered end has deposited thereon a reflecting material, and the rod is so aligned that light is transmitted from the first channel in a first direction across the face of said second channel in the probe which lies in a plane perpendicular to the longitudinal direction and wherein the second channel is arranged to receive light in a direction generally 90° displaced from said first direction.

23. An optical instrument according to claim 19 further comprising a tubular housing for securing said first and second channel means as a probe wherein said probe terminates, at the measurement end, in a transparent axially extending plate which contains a diametrical opaque insert which extends through the thickness of the plate, and said plate is aligned in the probe so that the opaque insert lies in a plane between light-conducting means of each channel.

24. In an instrument according to claim 19 where said measuring means includes a photo multiplier.

25. In an instrument according to claim 19 where said gating control means can achieve a mark space ratio of 1:22,000.

* * * * *